United States Patent
Choi et al.

(10) Patent No.: US 10,221,187 B2
(45) Date of Patent: Mar. 5, 2019

(54) METHOD FOR PREPARING ANHYDROSUGAR ALCOHOL USING TWO-STEP HYDROTHERMAL REACTION

(71) Applicant: SK Innovation Co., Ltd., Seoul (KR)

(72) Inventors: Young Bo Choi, Seoul (KR); Sung Real Son, Daejeon (KR); In Hyoup Song, Daejeon (KR); Sang Il Lee, Daejeon (KR); Sang Hyun Cho, Daejeon (KR); Dae Hyun Choo, Busan (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 15/511,285

(22) PCT Filed: Sep. 15, 2015

(86) PCT No.: PCT/KR2015/009676
§ 371 (c)(1),
(2) Date: Mar. 15, 2017

(87) PCT Pub. No.: WO2016/043501
PCT Pub. Date: Mar. 24, 2016

(65) Prior Publication Data
US 2017/0253608 A1    Sep. 7, 2017

(30) Foreign Application Priority Data

Sep. 16, 2014 (KR) .................. 10-2014-0122904

(51) Int. Cl.
| | | |
|---|---|---|
| *C07D 493/04* | (2006.01) | |
| *C07D 309/10* | (2006.01) | |
| *C07D 307/20* | (2006.01) | |
| *B01J 27/053* | (2006.01) | |
| *B01J 27/138* | (2006.01) | |

(52) U.S. Cl.
CPC .......... *C07D 493/04* (2013.01); *B01J 27/053* (2013.01); *B01J 27/138* (2013.01); *C07D 307/20* (2013.01); *C07D 309/10* (2013.01)

(58) Field of Classification Search
CPC .. C07D 493/04; C07D 309/10; C07D 307/20; B01J 27/053; B01J 27/138
See application file for complete search history.

(56) References Cited

U.S. PATENT DOCUMENTS

| 7,420,067 B2* | 9/2008 | Sanborn ............... C07D 307/02 549/464 |
|---|---|---|
| 2007/0173651 A1 | 7/2007 | Holladay et al. |
| 2009/0259057 A1 | 10/2009 | Schreck et al. |

FOREIGN PATENT DOCUMENTS

| KR | 1020140048435 A | 4/2014 |
|---|---|---|
| KR | 1020140048438 A | 4/2014 |
| KR | 1020140105183 A | 9/2014 |

OTHER PUBLICATIONS

Periodic Table of the Elements Vertex42.com 2011; p. 1.*
De Almeida et al., Cellulose Conversion to Isosorbide in Molten Salt hydrate Media, ChemSusChem, 2010, pp. 325-328, vol. 3.
Fleche et al., Isosorbide Preparation, Properties and Chemistry, Starch/Starke, 1986, pp. 26-30, vol. 38, No. 1.
Yamaguchi et al., Sorbitol dehydration in high temperature liquid water, Green Chemistry, 2011, pp. 873-881, vol. 13.

* cited by examiner

*Primary Examiner* — John M Mauro
(74) *Attorney, Agent, or Firm* — The Webb Law Firm

(57) ABSTRACT

A method for producing anhydrosugar alcohol according to the present invention can increase the yield of anhydrosugar alcohol even in the absence of a catalyst or in the presence of a small amount of a transition metal salt catalyst by controlling the temperature of a high-temperature reaction, which converts sugar alcohol to anhydrosugar alcohol, in two steps, that is, a first low-temperature reaction step and a second high-temperature reaction step.

20 Claims, 3 Drawing Sheets

METHOD FOR PREPARING ANHYDROSUGAR ALCOHOL USING TWO-STEP HYDROTHERMAL REACTION

CROSS-REFERENCE TO RELATED APPLICATIONS

This application is the United States national phase of International Application No. PCT/KR2015/009676 filed Sep. 15, 2015, and claims priority to Korean Patent Application No. 10-2014-0122904 filed Sep. 16, 2014, the disclosures of which are hereby incorporated in their entirety by reference.

TECHNICAL FIELD

The present invention relates to a method for producing anhydrosugar alcohol, and more particularly to a method for producing anhydrosugar alcohol, which can economically increase the yield of anhydrosugar alcohol even in the absence of a catalyst or in the presence of a small amount of a transition metal salt catalyst by controlling the temperature of a high-pressure reaction, which converts sugar alcohol to anhydrosugar alcohol, in two steps, that is, a first low-temperature reaction step and a second high-temperature reaction step.

BACKGROUND ART

Due to the exhaustion of traditional energy sources together with an increase in the global energy demand, impetus is currently being given to the development of alternative energy sources. Among them, biomass is renewable quantitative biological resource that attracts a great deal of attention.

Among biomass-based industrial raw materials, isosorbide ($C_6H_{10}O_4$) that is prepared by dehydration of sorbitol ($C_6H_{14}O_6$) attracts attention as an environmentally friendly raw material for preparing polycarbonate (PC) as a substitute for bisphenol A (BPA), an epoxy monomer or an environmentally friendly plasticizer. Namely, isosorbide, a material that can be obtained by simple dehydration of sorbitol, is attracting attention as a monomer required for synthesis of next-generation, high-performance, environmentally friendly materials that can replace conventional polymer products, and many studies thereon have been conducted.

Environmentally friendly materials generally show poor properties compared to petrochemical-based materials, whereas isosorbide advantages in that it is environmentally friendly and, at the same time, shows excellent properties compared to conventional petrochemical-based materials. In addition, isosorbide serving as an agent for treating cardiac diseases may also be used as an additive that can make plastic materials stronger and tougher.

When D-glucose obtained from biomass by pretreatment is hydrogenated in the presence of a catalyst, sorbitol is produced. Isosorbide is produced by double dehydration of sorbitol. This cyclization reaction is influenced by various reaction conditions, including temperature, pressure, solvent, catalyst, etc.

Currently, as a method of preparing isosorbide from sorbitol, a process (Roquette process (France): G. Fleche, M. H. Lestrem, starch/starke 1986, 38, 26-30) is widely used in which sulfuric acid is used as a catalyst and a reaction is carried out under a reduced pressure of about 10 mmHg. However, when a liquid strong acid catalyst such as sulfuric acid is used, a reactor is easily corroded, and for this reason, an expensive reactor should be used. In addition, an additional process such as pH neutralization is required, and it is difficult to treat waste. Furthermore, a large amount of energy is continuously consumed to maintain a high vacuum level of about 10 mmHg, and thus the operating cost for the reaction is high. For this reason, a method employing molten salt hydrate (ChemSusChem. 2010, 3, 325-328) and the like have recently been proposed. However, this preparation method has problems in that, because molten salt hydrate should be used in very large amounts compared to the reactant sorbitol, the method is cost-ineffective and is not easy to commercialize.

Thus, if an efficient method for preparing and separating isosorbide is developed and a mass production process based on this method is provided so that a sufficiently inexpensive raw material (isosorbide) can be obtained, the demand for isosorbide as an industrial product can be increased.

Accordingly, the present inventors have found that, when the temperature of a high-pressure reaction that converts sorbitol to isosorbide is controlled in two steps, that is, a first low-temperature reaction step and a second high-temperature reaction step, in view of the fact that the rate of a latter-step reaction that converts the intermediate product 1,4-sorbitan ($C_6H_{12}O_5$; 1,4-anhydro-sorbitol or 1,4-AHSO) to isosorbide is lower than the rate of a former-step reaction that converts sorbitol to 1,4-sorbitan in a high-pressure reaction that converts sorbitol to isosorbide, the yield of isosorbide in the high-pressure reaction can be economically increased even in the absence of a catalyst or in the presence of a small amount of a transition metal salt catalyst, thereby completing the present invention.

SUMMARY OF INVENTION

It is an object of the present invention to provide a method for producing anhydrosugar alcohol, which can economically increase the yield of anhydrosugar alcohol in a reaction that converts sugar alcohol into anhydrosugar alcohol.

DETAILED DESCRIPTION OF THE INVENTION

To achieve the above objects, the present invention provides a method of producing anhydrosugar alcohol using a two-step hydrothermal reaction in the absence of a catalyst, the method comprising subjecting an aqueous solution of sugar alcohol to a first reaction at a temperature of 240° C. to 285° C. followed by a second reaction at a temperature of 286° C. to 340° C.

The present invention also provides a method of producing anhydrosugar alcohol in the presence of a transition metal salt catalyst, the method comprising subjecting an aqueous solution of sugar alcohol to a first reaction at a temperature of 240° C. to 285° C. followed by a second reaction at a temperature of 300° C. to 340° C.

BEST MODE FOR CARRYING OUT THE INVENTION

Figure 1:
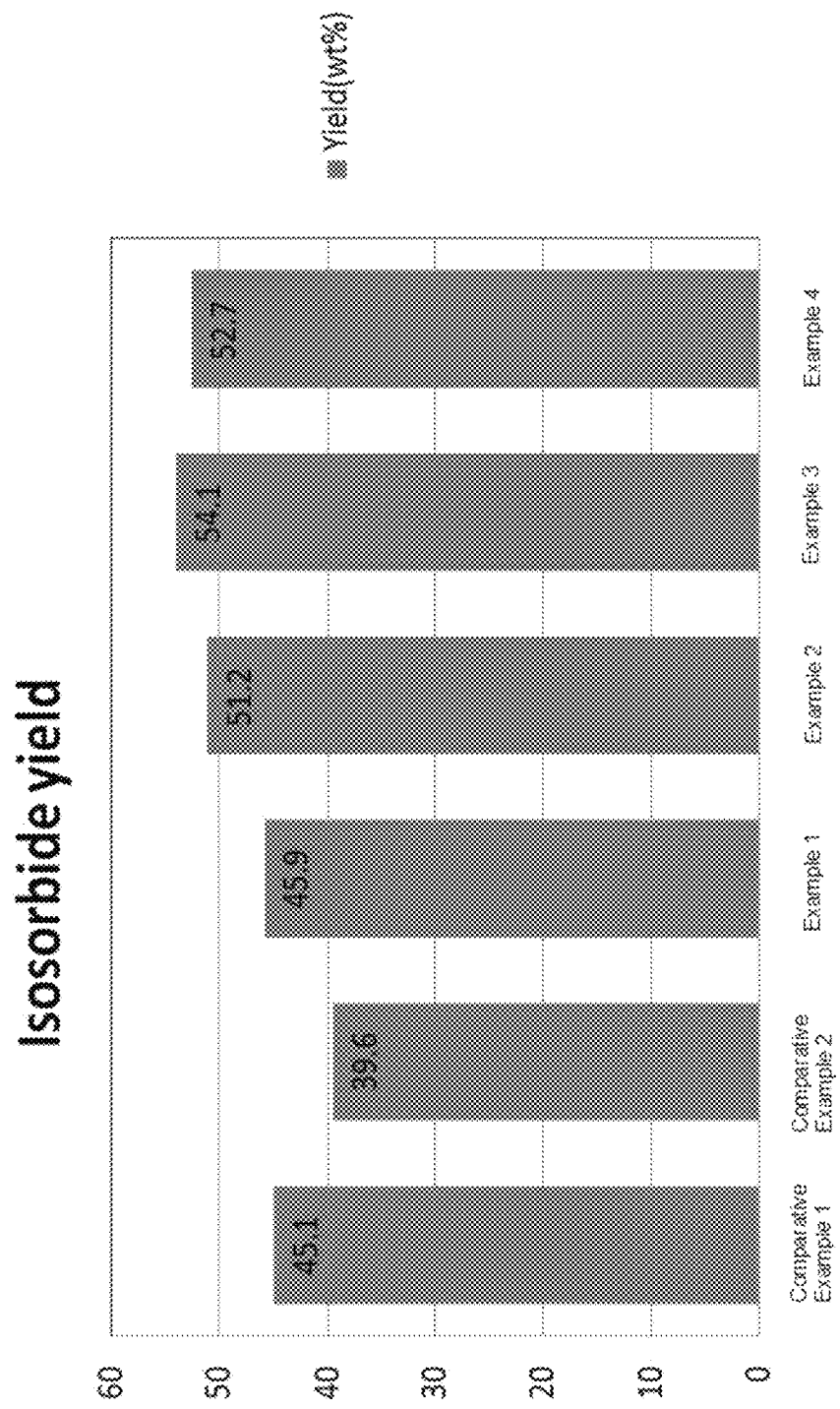
FIG. 1 is a graph showing the yield of isosorbide prepared according to an embodiment of the present invention.

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, in view of the fact that the rate of a latter-step reaction that converts the intermediate product 1,4-sorbitan to isosorbide is lower than the rate of a former-step reaction that converts sorbitol to 1,4-sorbitan in a reaction that converts sorbitol to isosorbide, the temperature of the reaction carried out in the absence of a catalyst was controlled in two steps, that is, a first low-temperature reaction step and a second high-temperature reaction step. As a result, the formation of 1,4-sorbitan that is produced at a high rate could be maximized through the first low-temperature reaction, the rate of the latter-step reaction that produces D-isosorbide from 1,4-sorbitan can be increased in the second high-temperature reaction performed at an increased reaction temperature, thereby increasing the yield of isosorbide.

A reaction that produces isosorbide by dehydration of sorbitol is shown in the following Reaction Scheme 1:

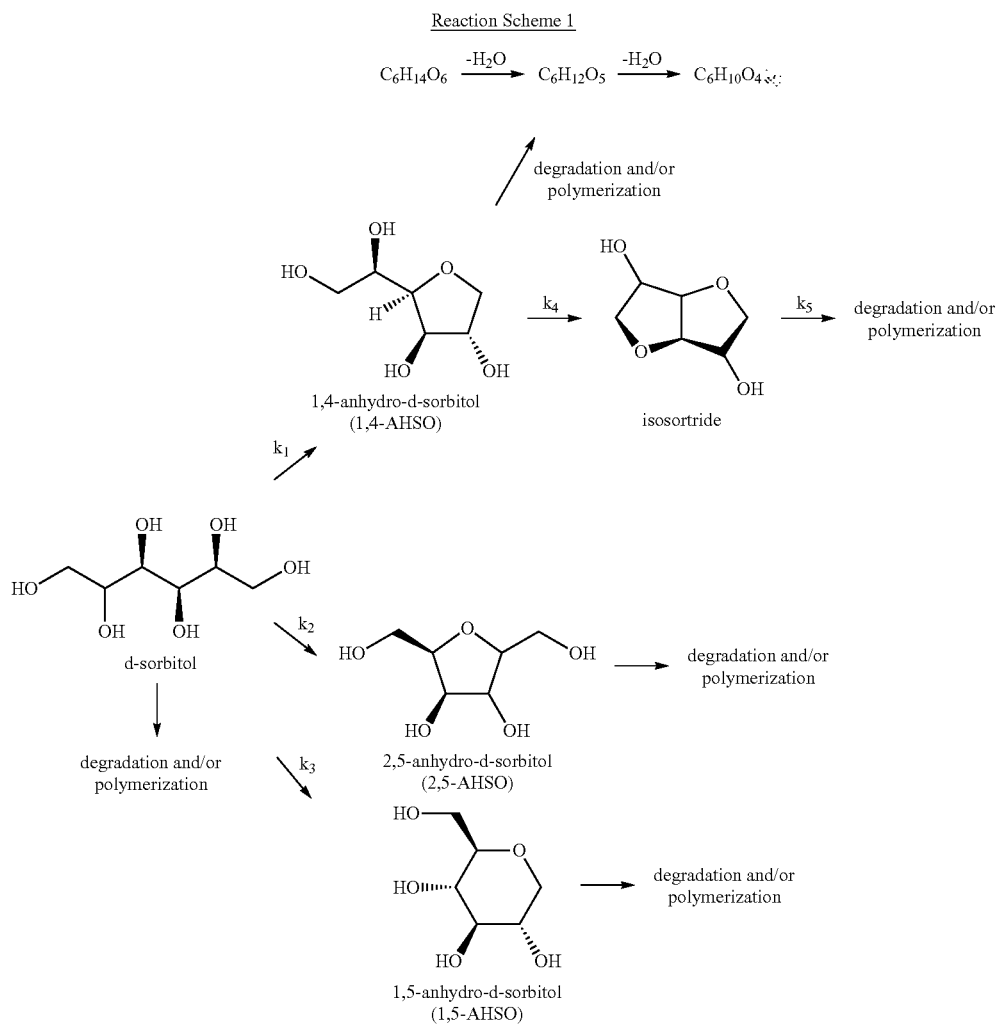

Reaction Scheme 1

In reaction scheme 1 above, a preferred path consists of a two-step reaction in which one water molecule is removed from D-sorbitol to produce 1,4-sorbitan, after which one water molecule is removed from 1,4-sorbitan to produce D-isosorbide. However, the rate of the reaction that produces 1,4-sorbitan from D-sorbitol is higher than the rate of the reaction that produces D-isosorbide from 1,4-sorbitan. Therefore, when the reaction temperature is controlled, the formation of 1,4-sorbitan can be maximized at a low temperature lower than 285° C. Side reactions that produce 2,5-sorbitan or 1,5-sorbitan from D-sorbitol or that degrade or polymerize D-sorbitol are promoted at a high temperature equal to higher than 285° C.

Green Chem. A. Yamaguchi et al., 13, 873 (2011) discloses a process of producing isosorbide using a phenomenon in which water is self-ionized at high temperature to reduce pH, without using a reduced-pressure process and a catalyst. However, this production process has disadvantages over conventional processes in that the yield of isosorbide is low and the reaction time is long. Thus, in order to develop a more economical process, it is required to increase the yield of isosorbide and shorten the reaction time. For such improvements, in the present invention, the formation of a 1,4-sorbitan intermediate that is produced at a high rate is maximized through the first low-temperature reaction, and the reaction that converts 1,4-sorbitan to D-isosorbide is promoted in the second high-temperature reaction that is carried out at an increased reaction temperature, thereby increasing the yield of isosorbide. In order to maximize the formation of 1,4-sorbitan and inhibit side reactions, the reaction time or residence time of the high-temperature reaction is preferably shorter than that of the low-temperature reaction.

Specifically, in one aspect, the present invention is directed to a method of producing anhydrosugar alcohol using a two-step hydrothermal reaction, the method comprising subjecting an aqueous solution of sugar alcohol to a first reaction at a temperature of 240° C. to 285° C. in the absence of a catalyst, followed by a second reaction at a temperature of 286° C. to 340° C.

The temperature of the first reaction may preferably range from 250° C. to 280° C., and the temperature of the second reaction may range from 290° C. to 320° C. In this temperature range, the effect of increasing the yield of isosorbide is obtained. In addition, the temperature difference between the first reaction and the second reaction is preferably 15° C. to 60° C.

If the temperature of the first reaction is lower than 240° C., the reaction time or the residence time will be very long, and if the temperature of the first reaction is higher than 285° C., side reactions can be promoted to reduce the yield of isosorbide. Meanwhile, if the temperature of the second reaction is lower than 286° C., the reaction for the conversion of 1,4-sorbitan to isosorbide will not be sufficiently performed, and if the temperature of the second reaction is higher than 340° C., side reactions in which the produced isosorbide is degraded or polymerized will strongly occur so that the yield of isosorbide can decrease rather than increase.

In the present invention, the first reaction may be performed at a pressure of 35-75 bar, and the second reaction may be performed at a pressure of 76-150 bar. Although the reaction pressure may also be artificially formed using inert gas such as nitrogen or helium, the reaction may preferably be performed using an autogeneous pressure (self-generated pressure) which is generated when water contained in an aqueous solution of sugar alcohol reaches gas-liquid equilibrium at the reaction temperature. When the autogeneous pressure is used, the reaction may be performed at a pressure which is generated during heating to the reaction temperature after 50-90% (preferably 60-80%) of the reactor volume is filled with the reactant.

In the present invention, the reaction time of the first reaction may be longer than the reaction time of the second reaction. Preferably, the reaction time of the first reaction may be 2-12 hours, and the reaction time of the second reaction may be 1-8 hours. However, the times of the reactions are not particularly limited, as long as the reaction time of the first reaction is longer than the reaction time of the second reaction. When the reaction time of the first reaction is longer than the reaction time of the second reaction, there will be an advantage in that the formation of 1,4-sorbitan is maximized so that the yield of isosorbide in the second reaction is increased.

In the present invention, the anhydrosugar alcohol may be isosorbide, and the sugar alcohol may be sorbitol.

The preparation method of isosorbide according to the present invention may be performed in a batch or continuous fashion. If the preparation method according to the present invention is performed using a batch reactor, sorbitol may be reacted in a single reactor at the first reaction temperature, and then the temperature of the reactor may be increased to the second reaction temperature so that the second reaction may be performed continuously following the first reaction. The reaction time in the batch reaction can be controlled by controlling the times during which the first-step and second reaction temperatures are maintained.

Figure 2:
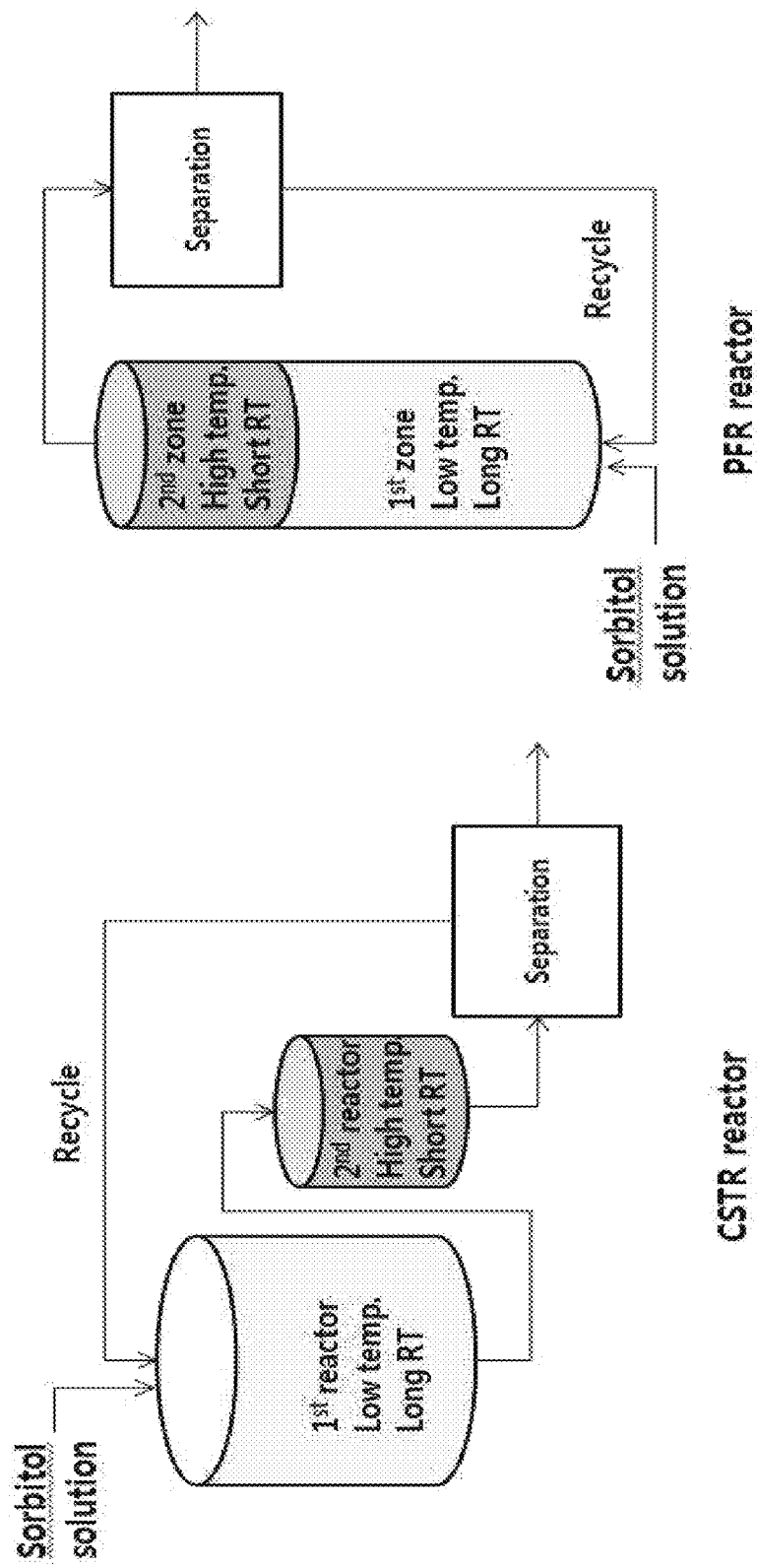
FIG. 2 schematically shows a reaction process that is carried out using reactors according to an embodiment of the present invention.

When the production method of the present invention is to be continuously performed, as shown in FIG. 2, the production method may be performed using a continuous stirred tank reactor (CSTR) or a plug flow reactor (PFR). The temperature and time of the continuous reaction can be controlled by controlling the temperatures and residence times of first- and second-step reactors.

The method for producing isosorbide according to the present invention may further comprise, after the second reaction, a step of separating and/or purifying a product. To perform the step of separating and/or purifying the product, distillation, crystallization and adsorption processes, etc., may be used alone or in combination of two or more.

Meanwhile, for separation and purification of the product, it is required to remove water used as a solvent for the reactant. For this removal of water, a large amount of energy is required. In the method for producing isosorbide according to the present invention, water can be removed without having to use energy, because water having a boiling point lower than that of sugar alcohol or anhydrosugar alcohol is easily evaporated when the pressure of the reactor is reduced to atmospheric pressure after completion of the second reaction which is performed at a pressure of 76-150 bar. Thus, the method of the present invention is very excellent in terms of energy efficiency and cost effectiveness.

The amount of water which can be removed through a reduced-pressure process and the amount of energy which is used for this removal can be controlled by controlling the temperature of the reduced-pressure process. For example, when the pressure of the second reaction is merely reduced to atmospheric pressure without using additional energy, about 40-80% of water can be removed. In addition, when a small amount of heat is supplied, 70-100% of water can be removed. Thus, the method for producing isosorbide according to the present invention has an advantage in that water can be removed in an economic manner.

In a method for producing isosorbide according to another embodiment of the present invention, a small amount of a transition metal salt may be used as a catalyst to relieve reaction conditions (reduce reaction temperature, reaction time and reaction pressure) to further increase the yield of isosorbide. The transition metal salt has advantages over acid catalysts in that it does not substantially corrode the reactor and is inexpensive. In addition, the transition metal salt does not affect the process of removing water under reduced pressure, because it has a high boiling point and is non-volatile.

Specifically, in another aspect, the present invention is directed to a method of producing anhydrosugar in the presence of a transition metal salt catalyst, the method comprising subjecting an aqueous solution of sugar alcohol to a first reaction at a temperature of 240° C. to 285° C. followed by a second reaction at a temperature of 300° C. to 340° C.

As the transition metal salt, a zinc, iron or magnesium salt, etc. may be used. More specific examples of the transition metal salt include zinc sulfide, zinc chloride, zinc nitrate, iron sulfide, iron chloride, iron nitrate, magnesium sulfide, magnesium chloride, magnesium nitrate and the like.

The transition metal salt is preferably used in an amount of 0.1-4 parts by weight based on 100 parts by weight of sorbitol. If the amount of transition metal salt used is less than 0.1 parts by weight, the effects of relieving reaction conditions and increasing the yield of isosorbide by addition of the catalyst will hardly be obtained, and If the amount of transition metal salt used is more than 4 parts by weight, cost-effectiveness will be reduced and side reactions will increase.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Temperature Control in Two Steps 100 g of a 50 wt % aqueous solution of D-sorbitol (Aldrich) was introduced into an autoclave reactor and reacted with stirring at 280° C. for 4 hours. Then, the temperature of the reactor was increased to 300° C., followed by an additional reaction for 3 hours. The reaction temperature was increased at a rate of 4° C./min. The pressure of the first reaction performed at 280° C. was about 65 bar, and the pressure of the second reaction performed at 300° C. was about 100 bar.

After the completion of the reaction, the obtained reaction product was diluted 20-fold with water and analyzed by high-performance liquid chromatography (HPLC, Agilent; equipped with a carbohydrate column). The yield of the isosorbide produced was 45.9 wt (57.2 mol %).

Example 2: Temperature Control in Two Steps

The procedure of Example 1 was repeated, except that 95 g of a 50 wt % aqueous solution of D-sorbitol (Aldrich) was used and the temperature increase from 280° C. to 300° C. was performed at a rate of 1° C./min. The yield of isosorbide produced was 51.2 wt % (63.8 mol %).

Example 3: Temperature Control in Two Steps and Use of Zinc Chloride ($ZnCl_2$) Catalyst 90 g of a 70 wt % aqueous solution of D-sorbitol (Aldrich) and 1.26 g (2 wt % based on the weight of D-sorbitol) of zinc chloride were introduced into an autoclave reactor and allowed to react with stirring at 250° C. for 2 hours. Then, the temperature of the reactor was increased to 300° C., followed by an additional reaction for 30 minutes. The reaction temperature was increased at a rate of 1° C./min. The pressure of the first reaction performed at 250° C. was about 45 bar, and the pressure of the second reaction performed at 300° C. was about 95 bar.

After the completion of the reaction, the obtained reaction product was diluted 20-fold with water and analyzed by high-performance liquid chromatography (HPLC, Agilent; equipped with a carbohydrate column). The yield of the isosorbide produced was 54.1 wt (67.4 mol %).

Example 4: Temperature Control in Two Steps and Use of Zinc Sulfide ($ZnSO_4$) Catalyst 90 g of a 70 wt % aqueous solution of D-sorbitol (Aldrich) and 2.25 g of zinc sulfide heptahydrate (zinc sulfide in an amount of 2 wt % based on the weight of D-sorbitol) were introduced into were introduced into an autoclave reactor and allowed to react with stirring at 250° C. for 2 hours. Then, the temperature of the reactor was increased to 300° C., followed by an additional reaction for 1 hour. The reaction temperature was increased at a rate of 1° C./min. The pressure of the first reaction performed at 250° C. was about 46 bar, and the pressure of the second reaction performed at 300° C. was about 97 bar.

After the completion of the reaction, the obtained reaction product was diluted 20-fold with water and analyzed by high-performance liquid chromatography (HPLC, Agilent; equipped with a carbohydrate column). The yield of the isosorbide produced was 52.7 wt (65.7 mol %).

Comparative Example 1: Isothermal Reaction 100 g of a 50 wt % aqueous solution of D-sorbitol (Aldrich) was introduced into an autoclave reactor and reacted with stirring at 300° C. for 4 hours. The pressure of the reaction was about 93 bar.

After the completion of the reaction, the obtained reaction product was diluted 20-fold with water and analyzed by high-performance liquid chromatography (HPLC, Agilent; equipped with a carbohydrate column). The yield of the isosorbide produced was 45.1 wt (56.2 mol %).

Comparative Example 2: Isothermal Reaction

The procedure of Comparative Example 1 was repeated, except that 90 g of a 50 wt % aqueous solution of D-sorbitol (Aldrich) was used and reacted at 280° C. for 6.5 hours. The pressure of the reaction was about 65 bar. The yield of the isosorbide produced was 39.6 wt (49.3 mol %).

The yields of the products obtained in Examples 1 to 4 and Comparative Examples 1 and 2 are shown in Table 1 below.

TABLE 1

| | Temperature and time | Pressure | Catalyst | Yield of products (wt %) | Yield of products (mol %) |
|---|---|---|---|---|---|
| Example 1 | Temperature control in two steps (280° C., 4 h → 300° C., 3 h) | 65 bar --> 100 bar | — | 45.9 | 57.2 |
| Example 2 | Temperature control in two steps (280° C., 4 h → 300° C., 3 h) | 65 bar --> 100 bar | — | 51.2 | 63.8 |
| Example 3 | Temperature control in two steps (250° C., 2 h → 300° C., 30 min) | 45 bar --> 95 bar | $ZnCl_2$ | 54.1 | 67.4 |
| Example 4 | Temperature control in two steps | 46 bar --> 97 bar | $ZnSO_4$ | 52.7 | 65.7 |

TABLE 1-continued

| | Temperature and time | Pressure | Catalyst | Yield of products (wt %) | Yield of products (mol %) |
|---|---|---|---|---|---|
| Comp. Ex. 1 | (250° C., 2 h → 300° C., 1 h) Isothermal (300° C., 4 h) | 93 bar | — | 45.1 | 56.2 |
| Comp. Ex. 2 | Isothermal (280° C., 6.5 h) | ~65 bar | — | 39.6 | 49.3 |

As can be seen in Table 1 above, the yields of isosorbide produced in Examples 1 to 4 comprising the two-step temperature control were significantly higher than those in Comparative Examples 1 and 2 performed by the isothermal reaction. Because the cost of the raw material sorbitol accounts for about 50% or more of the production cost of isosorbide, it can be seen that an increase in isosorbide yield of up to 18.1 mol % for a short reaction time corresponding to about 40% indicates a higher productivity and a significant economic gain.

Example 5: Simulation of Water Removal Under Reduced Pressure

Figure 3:
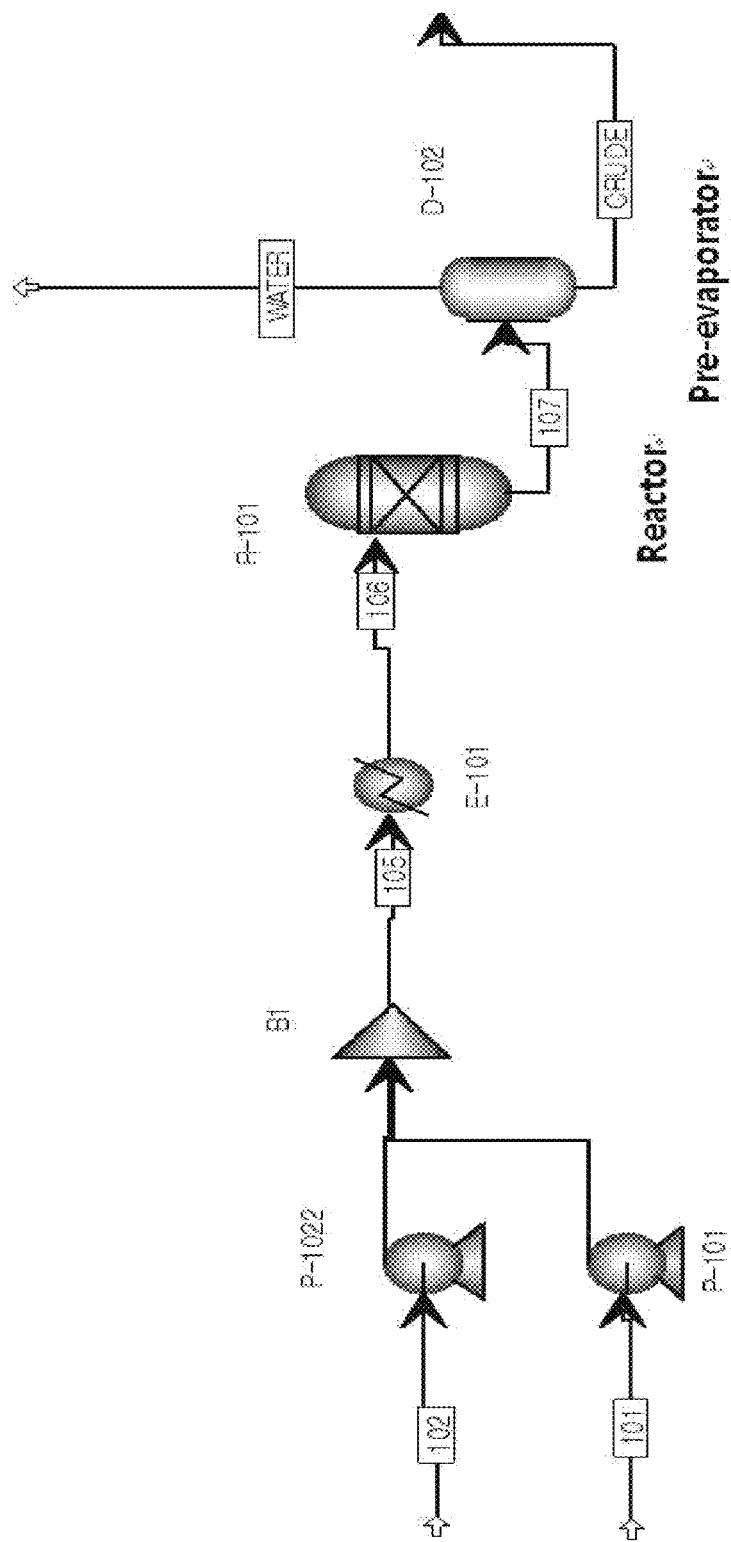
FIG. 3 schematically shows a process of removing water under reduced pressure according to an embodiment of the present invention.

Using the Aspen plus V8.2 program, the effect of a reduced-pressure process on water removal was simulated. The simulation scheme is shown in FIG. 3. When a reaction product having the composition shown in Table 2 below was obtained under the conditions of 300° C. and 80 bar, the amount of water removed from a pre-evaporator by a reduced-pressure process was calculated. In the simulation, 80 bar lower than actual reaction pressure was applied. The reason was to strictly evaluate the efficiency of the water removal process by changing pressure to form the conditions where water would be more difficult to evaporate. Thus, when actual reaction conditions are used, the efficiency of removal of water will be higher and the amount of energy required will also be smaller.

TABLE 2

Composition of Reaction Product Applied to Simulation

| Composition | wt % |
|---|---|
| Water | 59 |
| Sorbitol | 0.25 |
| Sorbitol by-product (including 1,4-AHSO, 2,5-AHSO and 1,5-AHSO) | 12.9 |
| isosorbide | 22.55 |
| Polymer by-product | 5.3 |

When a pre-evaporator was not additionally heated and the pressure of a reaction product with 300° C. and 80 bar was reduced to 1 bar, it was shown that about 60% of water contained in the reaction product was removed and that the temperature of the reaction product from which water was removed was reduced to about 116° C.

Example 6: Simulation of Water Removal Under Reduced Pressure

Using the same reaction product composition as described in Example 5, a case was simulated in which the pressure of a reaction product with 300° C. and 80 bar was reduced to 1 bar while a pre-evaporator was heated at a rate of about 70 cal/h-kg. It was shown that about 82% of water contained in the reaction product was removed and that the temperature of the reaction product from which water was removed was reduced to about 119° C.

Example 7: Simulation of Water Removal Under Reduced Pressure

Using the same reaction product composition as described in Example 5, a case was simulated in which the pressure of a reaction product with 300° C. and 80 bar was reduced to 1 bar while a pre-evaporator was maintained at a temperature of about 180° C. It was shown that about 99% or more of water contained in the reaction product was removed.

In the cases where water was removed under reduced pressure according to Examples 5 to 7, it was shown that the temperature of the reaction product was reduced and that up to 99% or more of water contained in the reaction product was removed.

INDUSTRIAL APPLICABILITY

As described above, in the method for producing anhydrosugar alcohol according to the present invention, the yield of anhydrosugar alcohol can be increased, and the operating cost can also be reduced, because the reaction by-product water can be easily removed without using a reduced-pressure process that requires a high operating cost. In addition, the equipment cost can be reduced, because an acid catalyst that corrodes a reactor is not used.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of preparing anhydrosugar alcohol in the absence of a catalyst, the method comprising subjecting an aqueous solution of sugar alcohol to a first reaction at a temperature of 240° C. to 285° C. followed by a second reaction at a temperature of 286° C. to 340° C., wherein temperature difference between the first reaction and the second reaction is 15° C. to 60° C.

2. A method of preparing anhydrosugar alcohol in the presence of a transition metal salt catalyst, the method comprising subjecting an aqueous solution of sugar alcohol to a first reaction at a temperature of 240° C. to 285° C. followed by a second reaction at a temperature of 300° C. to 340° C.

3. The method of claim 2, wherein the transition metal salt is a zinc salt, an iron salt, or a mixture thereof.

4. The method of claim 1, wherein the first reaction is performed at a pressure of 35-75 bar, and the second reaction is performed at a pressure of 76-150 bar.

5. The method of claim 1, wherein a pressure is reduced to an atmospheric pressure after completion of the second reaction to remove water from a second reaction product.

6. The method of claim 1, wherein a reaction time of the first reaction is longer than a reaction time of the second reaction.

7. The method of claim 1, wherein the anhydrosugar alcohol is isosorbide, and the sugar alcohol is sorbitol.

8. The method of claim 1, which is performed in a continuous stirred tank reactor (CSTR), a plug flow reactor (PFR) or a batch reactor (BR).

9. The method of claim 1, further comprising a step of separating a product after the second reaction.

10. The method of claim 2, wherein the first reaction is performed at a pressure of 35-75 bar, and the second reaction is performed at a pressure of 76-150 bar.

11. The method of claim 2, wherein a pressure is reduced to an atmospheric pressure after completion of the second reaction to remove water from a second reaction product.

12. The method of claim 2, wherein a reaction time of the first reaction is longer than a reaction time of the second reaction.

13. The method of claim 2, wherein the anhydrosugar alcohol is isosorbide, and the sugar alcohol is sorbitol.

14. The method of claim 2, which is performed in a continuous stirred tank reactor (CSTR), a plug flow reactor (PFR) or a batch reactor (BR).

15. The method of claim 2, further comprising a step of separating a product after the second reaction.

16. A method of preparing anhydrosugar alcohol in the presence of magnesium salt catalyst, the method comprising subjecting an aqueous solution of sugar alcohol to a first reaction at a temperature of 240° C. to 285° C. followed by a second reaction at a temperature of 300° C. to 340° C.

17. The method of claim 16, wherein the first reaction is performed at a pressure of 35-75 bar, and the second reaction is performed at a pressure of 76-150 bar.

18. The method of claim 16, wherein a pressure is reduced to an atmospheric pressure after completion of the second reaction to remove water from a second reaction product.

19. The method of claim 16, wherein a reaction time of the first reaction is longer than a reaction time of the second reaction.

20. The method of claim 16, further comprising a step of separating a product after the second reaction.

* * * * *